(12) United States Patent
Hall et al.

(10) Patent No.: US 8,702,644 B2
(45) Date of Patent: Apr. 22, 2014

(54) INSTRUMENT FOR DEBRIDING TISSUE AND APPLYING THERAPEUTIC CELLS

(75) Inventors: Steven G. Hall, Cincinnati, OH (US); John A. Hibner, Mason, OH (US); Julia J. Hwang, Wayland, MA (US); Yolanda F. Carter, Union, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 487 days.

(21) Appl. No.: 12/779,137

(22) Filed: May 13, 2010

(65) Prior Publication Data

US 2011/0282270 A1    Nov. 17, 2011

(51) Int. Cl.
*A61B 17/20* (2006.01)
*A61B 17/32* (2006.01)
*A61B 17/00* (2006.01)
*A61B 17/22* (2006.01)
*A61D 1/02* (2006.01)

(52) U.S. Cl.
USPC ............... 604/22; 606/83; 606/159; 606/170; 606/180

(58) Field of Classification Search
USPC .............. 604/22, 33–35, 49, 52–54, 118; 606/159–170, 171, 180, 83
See application file for complete search history.

(56) References Cited

U.S. PATENT DOCUMENTS

| | | | |
|---|---|---|---|
| 5,526,822 A | 6/1996 | Burbank et al. | |
| 5,694,951 A | 12/1997 | Bonutti | |
| 5,897,567 A * | 4/1999 | Ressemann et al. | 606/159 |
| 6,086,544 A | 7/2000 | Hibner et al. | |
| 6,990,982 B1 | 1/2006 | Bonutti | |
| 7,115,100 B2 | 10/2006 | McRury et al. | |
| 7,442,171 B2 | 10/2008 | Stephens et al. | |
| 7,611,473 B2 | 11/2009 | Boock et al. | |
| 7,959,608 B2 * | 6/2011 | Nash et al. | 604/155 |
| 2004/0078090 A1 | 4/2004 | Binette et al. | |
| 2004/0193071 A1 | 9/2004 | Binette et al. | |
| 2005/0038520 A1 | 2/2005 | Binette et al. | |

(Continued)

FOREIGN PATENT DOCUMENTS

| WO | WO 2006/124634 | 11/2006 |
|---|---|---|
| WO | WO 2008/051925 | 5/2008 |
| WO | WO 2008/103296 | 8/2008 |

OTHER PUBLICATIONS

International Search Report and Written Opinion dated Aug. 26, 2011 for Application No. PCT/US2011/036440.

(Continued)

*Primary Examiner* — Matthew F DeSanto
(74) *Attorney, Agent, or Firm* — Frost Brown Todd LLC

(57) ABSTRACT

A tissue treatment device comprises a housing having a chamber that receives a treatment fluid mixture of tissue morsels and a scaffold material. A debriding shaft including a plurality of cutters is coupled with the housing. The debriding shaft extends proximally within the chamber and extends distally from the end of the housing. The debriding shaft is inserted within a treatment site such as a fistula tract and is rotated and reciprocated such that the debriding shaft removes tissue cells along the site. The site is flushed with saline or other irrigating fluid followed by application of the treatment fluid mixture. The chamber of the housing comprises agitators positioned adjacent the debriding shaft. The treatment fluid mixture passes through the chamber of the housing along and between the outer surface of the debriding shaft and the agitators for thorough mixing before exiting the device at the treatment site.

17 Claims, 8 Drawing Sheets

(56) References Cited

U.S. PATENT DOCUMENTS

| | | |
|---|---|---|
| 2005/0113736 A1 | 5/2005 | Orr et al. |
| 2005/0125077 A1 | 6/2005 | Harmon et al. |
| 2005/0240146 A1* | 10/2005 | Nash et al. ............... 604/35 |
| 2008/0021486 A1* | 1/2008 | Oyola et al. ............. 606/169 |
| 2008/0071385 A1 | 3/2008 | Binette et al. |
| 2008/0161757 A1 | 7/2008 | Nayak et al. |
| 2008/0214955 A1 | 9/2008 | Speeg et al. |
| 2008/0234715 A1* | 9/2008 | Pesce et al. ............. 606/171 |
| 2008/0311219 A1 | 12/2008 | Gosiewska et al. |
| 2009/0299328 A1 | 12/2009 | Mudd et al. |
| 2010/0160819 A1 | 6/2010 | Parihar et al. |

OTHER PUBLICATIONS

U.S Appl. No. 12/483,305, Jun. 12, 2009, Hibner et al.

* cited by examiner

US 8,702,644 B2

INSTRUMENT FOR DEBRIDING TISSUE AND APPLYING THERAPEUTIC CELLS

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, ure-thro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments,"published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, and issued Jan. 25, 2011 as U.S. Pat. No. 7,875,296, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, and issued Sep. 14, 2010 as U.S. Pat. No. 7,794,408, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, and issued Oct. 11, 2011 as U.S. Pat. No. 8,034,003, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, and issued Mar. 8, 2011 as U.S. Pat. No. 7,901,461, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
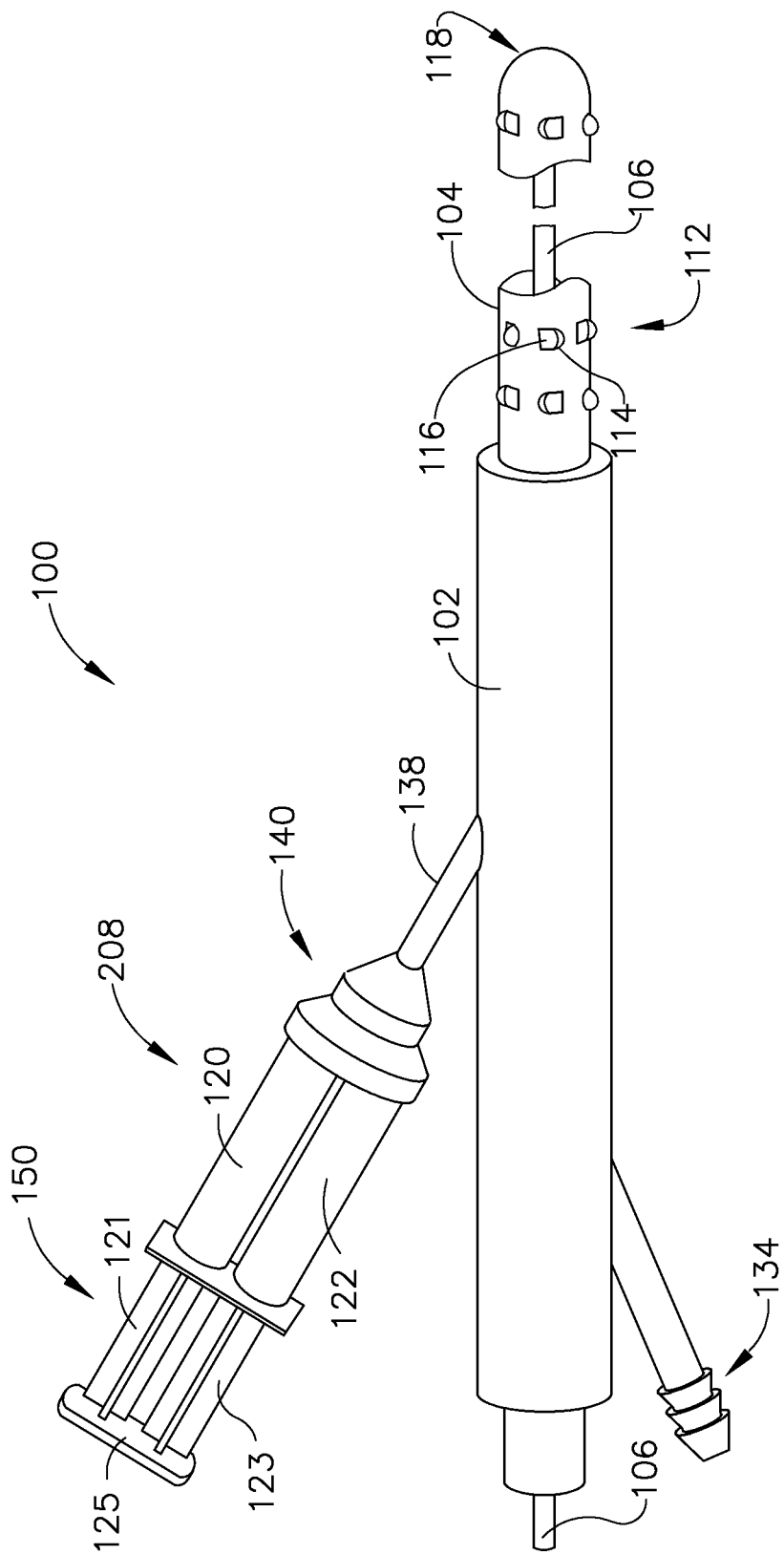
FIG. 1 depicts a perspective view of an exemplary tissue treatment device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to harvest tissue, mince or morcellate tissue, mix tissue particles with other medical fluid components, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly(amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL®(Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat, No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, and issued Oct. 28, 2008 as U.S. Pat. No. 7,442,171; U.S. Pub. No. 2008/0214955, entitled "Presentation of Biopsy Sample by Biopsy Device," published Sep. 4, 2008; U.S. non-provisional patent application Ser. No. 12/337,942, entitled "Biopsy Device with Central Thumbwheel," filed Dec. 18, 2008, and published Jun 24, 2010 as U.S. Pub. No. 2010/0160819; and U.S. non-provisional patent application Ser. No. 12/483,305, entitled "Tetherless Biopsy Device with Reusable Portion," filed Jun. 12, 2009, and issued Jun. 26, 2012 as U.S. Pat. No. 8,206,316. The disclosure of each of the above-cited U.S. Patents, U.S. Patent Application Publications, and U.S. Non-Provisional Patent Applications is incorporated by reference herein. Such biopsy devices may be used to extract a plurality of tissue specimens from one or more sites in a single patient. It should also be understood that any suitable device described in any other reference that is cited herein may be used to harvest tissue. Additional examples of devices that may be used to harvest tissue will be described in greater detail below. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 mm$^3$ and approximately 2 mm$^3$; or more particularly between approximately 0.05 mm$^3$ and approximately 1 mm$^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), polyvinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly (ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. Merely illustrative examples of how the walls of a fistula may be treated and how a medical fluid may be applied in a fistula will be described in greater detail below. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Tissue Treatment Device with Distal Apertures

Figure 2:
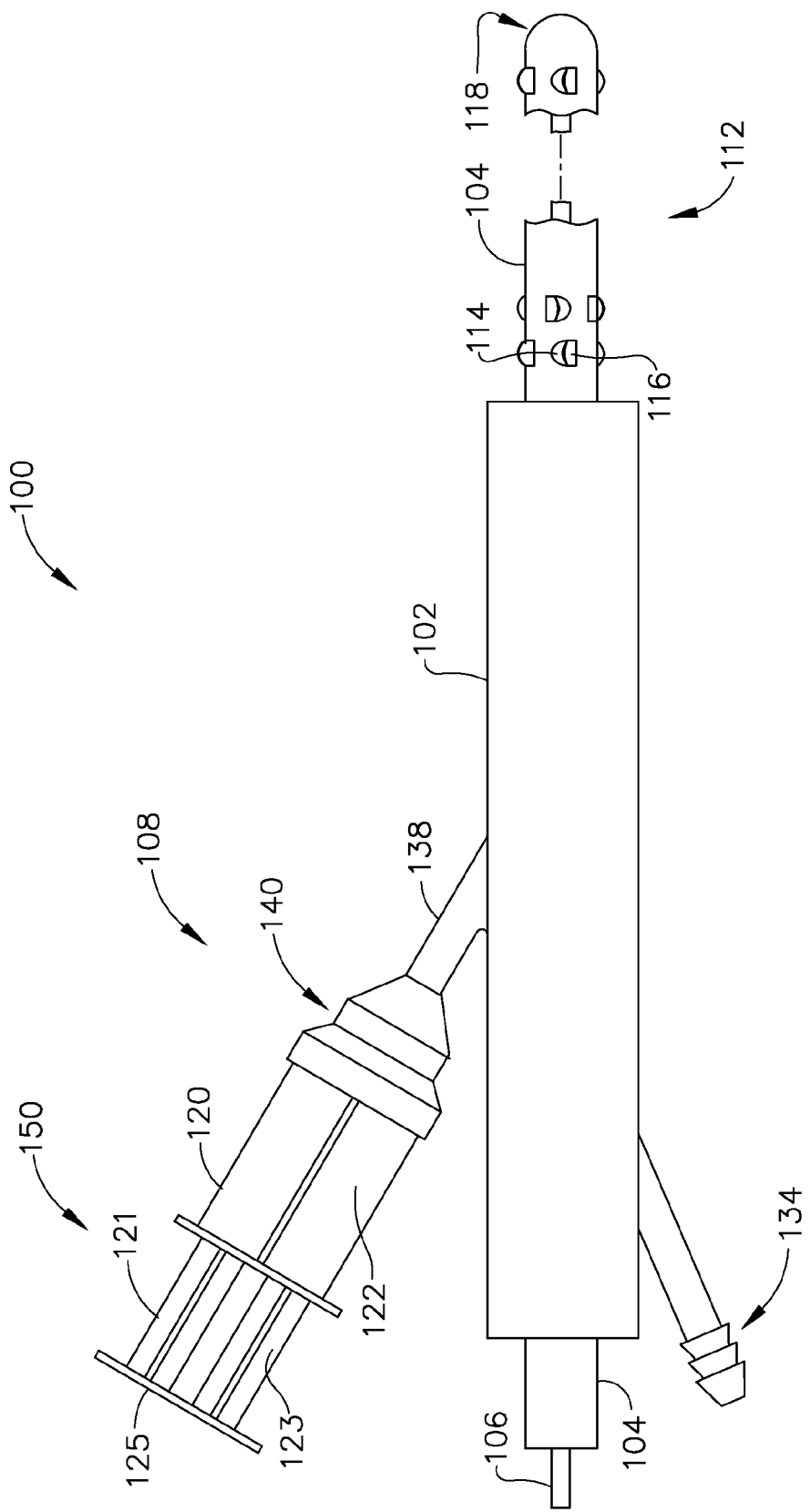
FIG. 2 depicts a side view of the device of FIG. 1.
Figure 3:
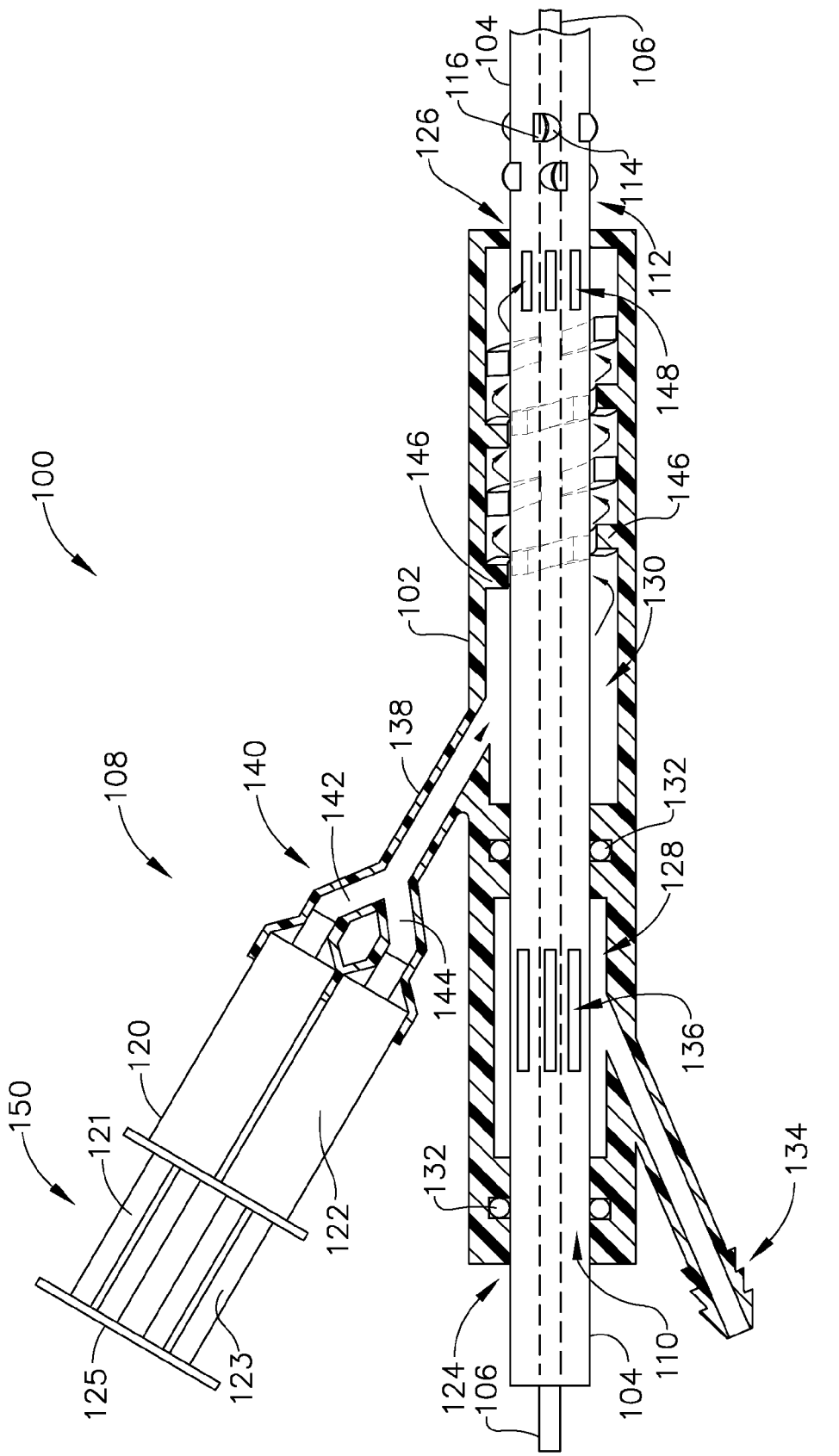
FIG. 3 depicts a side view of the device of FIG. 2, with the housing shown in cross section.
Figure 4:
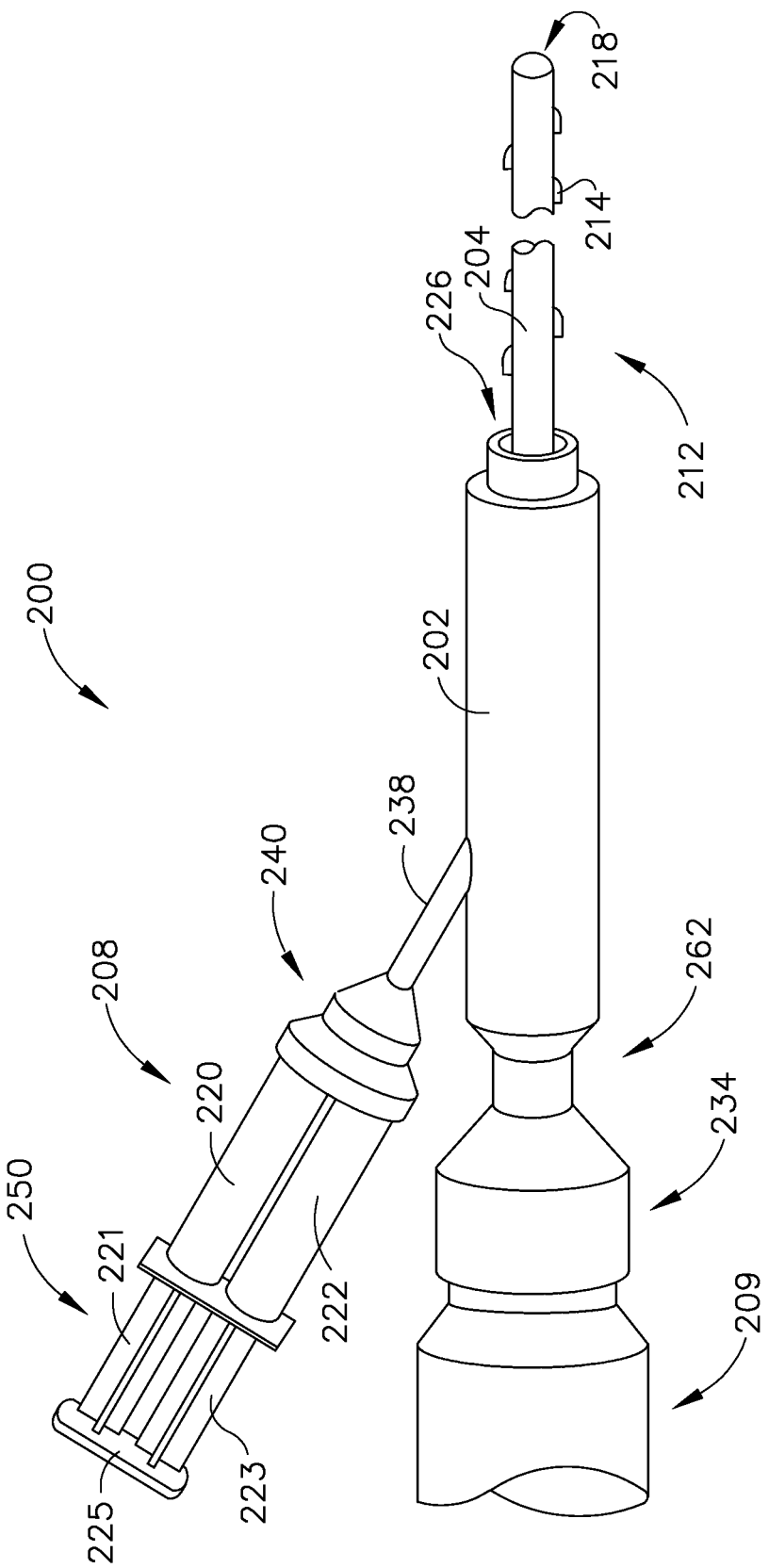
FIG. 4 depicts a perspective view of another exemplary tissue treatment device.
Figure 5:
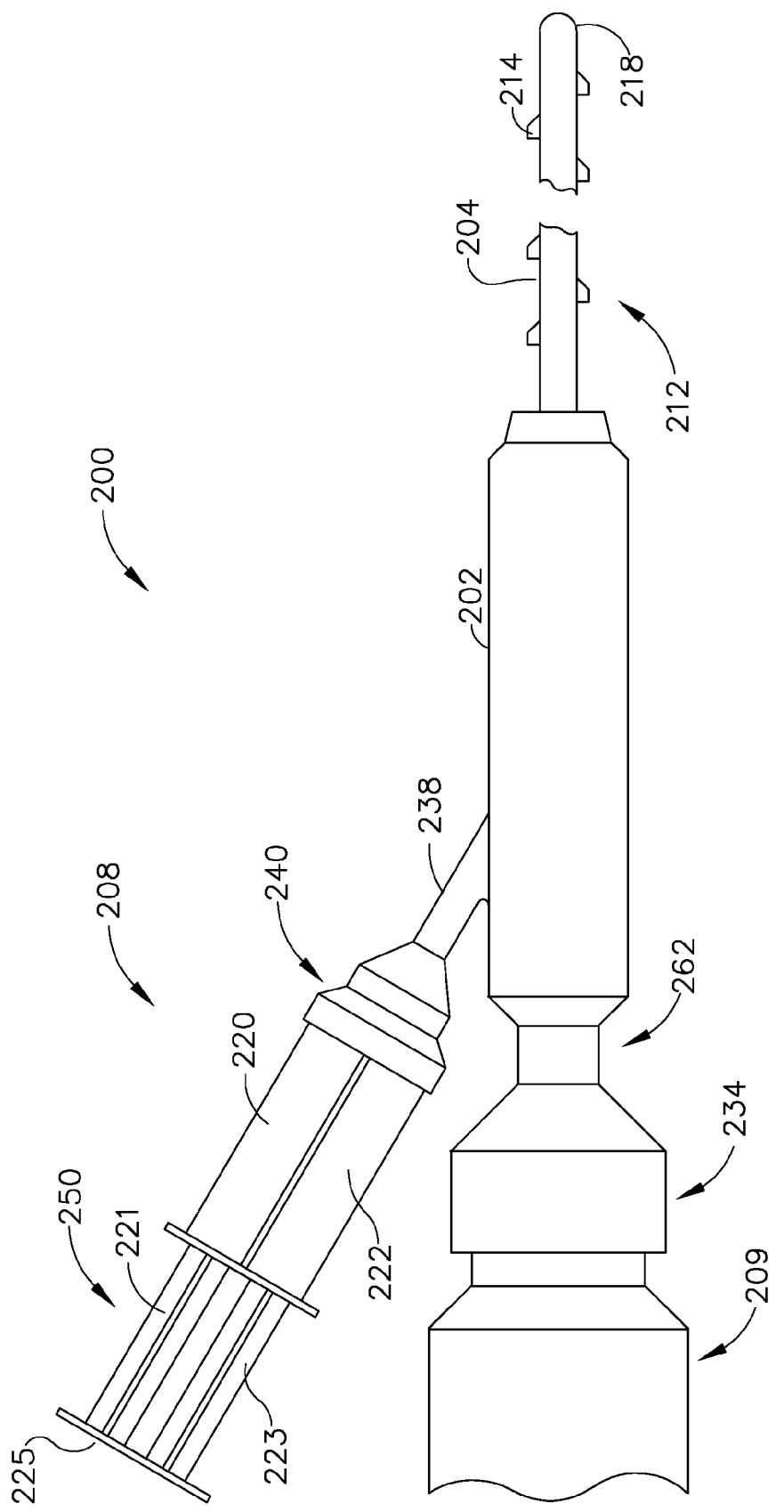
FIG. 5 depicts a side view of the device of FIG. 4.

FIGS. 1-3 depicts an exemplary tissue treatment device (100). Device (100) comprises a housing (102), a debriding shaft (104), a central shaft (106), and a syringe assembly (108). These components and their sub-components will be described in greater detail below. As will also be described in greater detail below, tissue treatment device (100) may be used to debride a fistula and administer a therapeutic mixture of biological material to the fistula to treat the fistula. It should be understood, however, that tissue treatment device (100) may be used in a variety of other ways and in a variety of other settings and procedures.

As shown in FIGS. 1-3, debriding shaft (104) of the present example comprises a proximal portion (110) and a distal portion (112). Distal portion (112) includes a plurality of cutters (114) that are operable for removing tissues and cells from a treatment site (e.g., in a fistula, etc.) in preparation for the site to receive a treatment as will be discussed in greater detail below. As shown in FIGS. 1 and 2, cutters (114) are configured as cup-like members that protrude tangentially outwardly from debriding shaft (104). These protruding cup-like members have sharpened edges that are operable to remove tissue cells when device (100) is inserted to a treatment site and debriding shaft (104) rotated and/or reciprocated as will be discussed in greater detail below. As can be seen in FIGS. 1-3, cutters (114) are configured and arranged in alternating orientations based on the longitudinal position of cutters (114) along the length of debriding shaft (104). The alternating orientations of cutters (114) provide selective cutting/debriding by sets of cutters (114) based on the direction in which debriding shaft (104) is rotated about its longitudinal axis. In other words, cutters (114) in certain longitudinal regions of debriding shaft (104) cut/debride only when debriding shaft (104) is rotated in one direction about its longitudinal axis; while cutters (114) in other longitudinal regions of debriding shaft (104) cut/debride only when debriding shaft (104) is rotated in another direction about its longitudinal axis. Of course, cutters (114) may be arranged and configured such that they all cut/debride when debriding shaft (104) is rotated in one or two directions about its longitudinal axis. As yet another merely illustrative variation, cutters (114) may be configured to cut/debride tissue when debriding shaft (104) is translated along its longitudinal axis, in addition to cutting/debriding tissue when debriding shaft (104) is rotated about its longitudinal axis. Such cutters (114) may be configured to cut/debride tissue when debriding shaft (104) is translated distally along its longitudinal axis, when debriding shaft (104) is translated proximally along its longitudinal axis, and/or when debriding shaft (104) is reciprocated along its longitudinal axis.

Distal portion (112) of debriding shaft (104) further comprises a plurality of apertures (116) adjacent to cutters (114). Apertures (116) provide access to the interior of debriding shaft (104), and apertures (116) are operable to permit the passage of a fluid or a treatment mixture from within debriding shaft (104) to a treatment site as will be discussed in greater detail below. Thus, in the present example, debriding shaft (104) comprises a hollow interior and a closed distal end (118). Distal end (118) of the present example is blunt, such that insertion of distal end (118) into an anatomical lumen (e.g., a fistula, etc.) will not inflict significant trauma on the sidewall of the anatomical lumen. Alternatively, distal end (118) may have a variety of other configurations, including but not limited to a sharp configuration. As another merely illustrative example, debriding shaft (104) may comprise an open or partially open distal end instead of having a closed distal end (118). Other suitable features, components, and configurations of debriding shaft (104) will be apparent to those of ordinary skill in the art in view of the teachings herein.

Central shaft (106) extends proximally from the proximal portion (110) of debriding shaft (104). Central shaft (106) is selectively keyed to debriding shaft (104) such that when central shaft (106) and debriding shaft (104) are engaged, rotation of central shaft (106) causes corresponding rotation of debriding shaft (104). When central shaft (106) and debriding shaft (104) are disengaged, each may rotate independently relative to each other. In some other versions, central shaft (106) and debriding shaft (104) are fixedly secured to one another such that they are in constant engagement. Still in other versions, central shaft (106) may be omitted entirely. In the present example, with central shaft (106) selectively keyed to debriding shaft (104), such a selectively keyed configuration is achieved with a set of engaging spur gear teeth (not shown) where one set of gear teeth are integral with central shaft (106) and another set of gear teeth are integral with debriding shaft (104). These gear teeth may be moved from the engaged to disengaged position by translating central shaft (106) longitudinally relative to debriding shaft (104). For instance, when central shaft (106) is moved distally relative to debriding shaft (104), the sets of gear teeth would mesh such that debriding shaft (104) rotates in unison with central shaft (106). When central shaft (106) is retracted proximally relative to debriding shaft (104), the sets of gear teeth would disengage from each other such that debriding shaft (104) and central shaft (106) rotate independent of one another. Of course, a variety of other structures or features may be used to provide selective keying of central shaft (106) with debriding shaft (104), including but not limited to a complementary key and keyway, etc. Still other suitable configurations for selectively keying central shaft (106) and debriding shaft (104) will be apparent to those of ordinary skill in the art in view of the teachings herein. It should also be understood that debriding shaft (104) may be selectively keyed with housing (102) in various ways, including but not limited to those described above for selectively keying central shaft (106) with debriding shaft (104).

In the present example, central shaft (106) is rotated manually. Alternatively, tissue treatment device (100) may include a motor (e.g., electric, pneumatic, etc.) that may be used to rotate central shaft (106) in addition to or in lieu of providing manual rotation of central shaft (106). While central shaft (106) is itself grasped and rotated in the present example, central shaft (106) is coupled with another structure to facilitate manual rotation of central shaft (106) in some other versions. For instance, central shaft (106) may be coupled with a rotating knob. Other suitable structures that may be coupled with central shaft (106) to facilitate manual rotation of central shaft (106) will be apparent to those of ordinary skill in the art in view of the teachings herein. It should also be understood that any of the rotation techniques and/or structures used with central shaft (106) may also be operable to provide rotation of debriding shaft (104). For instance, debriding shaft (104) may be rotated manually or by a motor when not keyed to central shaft (106). In some other versions, debriding shaft (104) may be coupled with some other rotation structure, such as a knob, to achieve rotation of debriding shaft (104) when debriding shaft (104) is not keyed to central shaft (106).

Syringe assembly (108) of the present example comprises a dual syringe barrel configuration. In the present example, first syringe barrel (120) contains prepared tissue morsels, while second syringe barrel (122) contains a fibrin scaffold material. Of course, first and second syringe barrels (120, 122) may contain other fluids or mixtures. To the extent that syringe assembly (108) contains tissue morsels, such tissue morsels may be formed or derived at least in part from tissue that was harvested from the same patient in which device (100) is being used to treat a medical condition (e.g., a fistula, etc.). Syringe assembly (108) is in fluid communication with the interior of housing (102) via a port (138), such that the tissue morsels and fibrin scaffold mix may be injected into the interior of housing (102) to produce a treatment mixture as will be described further below. Syringe assembly (108) further comprises a first plunger (121) that translates within first syringe barrel (120); and a second plunger (123) that translates within second syringe barrel (122). A plunger actuator (125) is unitarily secured to both plungers (121, 123), such that both plungers (121, 123) may be actuated simultaneously by actuating plunger actuator (125). In some other versions, plungers (121, 123) may be actuated independently of each other.

As best seen in FIG. 3, housing (102) of the present example has an open proximal end (124) and an open distal end (126). Housing (102) further defines a proximal chamber (128) and a distal chamber (130). An o-ring (132) separates proximal and distal chambers (128, 130). Another o-ring fluidly isolates proximal chamber (128) from open proximal end (124). Debriding shaft (104) extends longitudinally through housing (102), and further extends proximally from open proximal end (124) of housing (102) and distally from open distal end (126) of housing (102). Debriding shaft (104) passes through proximal chamber (128) and distal chamber (130). In the present example, o-rings (132) encircle debriding shaft (104) while still permitting debriding shaft (104) to rotate. In some versions, debriding shaft (104) may be configured with a flange along proximal portion (110), where the flange is configured to abut housing (102) at open proximal end (124) of housing (102) such that the flange restricts or prevents longitudinal translation of debriding shaft (104) in the distal direction. Similarly, debriding shaft (104) may be configured with a flange along distal portion (112), where this flange is configured to abut housing (102) at open distal end (126) of housing (102) to restrict or prevent longitudinal translation of debriding shaft (104) in the proximal direction. Furthermore, such flanges may be fixed or removable for easy assembly and disassembly of device (100). Still other features, structures, and/or modifications to debriding shaft (104), housing (102), and/or other components, for restricting the longitudinal movement of debriding shaft (104) and/or for other purposes, will be apparent to those of ordinary skill in the art in view of the teachings herein.

Proximal chamber (128) of housing (102) is in fluid communication with port (134). In the present example, port (134) is configured for connection to an irrigation device for injecting an irrigating fluid into proximal chamber (128). For instance, in the present example, port (134) is connected to an irrigation device equipped with a saline fluid source. While the present example describes using an irrigating fluid with port (134), it will be apparent to those of ordinary skill in the art based on the teachings herein that other types of fluid (e.g., treatment fluids, etc.) may be communicated through port (134) and proximal chamber (128). In the present example, when the saline is injected within proximal chamber (128), the saline enters a plurality of first access windows (136) of debriding shaft (104). First access windows (136) are located along the length of debriding shaft (104) such that first access windows (136) are longitudinally positioned within proximal chamber (128). First access windows (136) provide access to the interior space of debriding shaft (104) such that the injected saline that enters the interior of debriding shaft (104) via first access windows (136) travels distally toward apertures (116). The injected saline ultimately discharges from the interior of debriding shaft (104) through apertures (116) to a treatment site. While port (134) has been described as being coupled with an irrigation device, port (134) may further be connected with a suction device, or a multi-function suction-irrigation device, such that in addition to irrigating the treatment site with saline, suction could be applied to remove debris from the site.

Distal chamber (130) of housing (102) is coupled with syringe assembly (108) by port (138). In the present example, port (138) branches into a dual-inlet assembly (140), where first inlet (142) is configured to receive first syringe barrel (120) and second inlet (144) is configured to receive second syringe barrel (122). As mentioned previously, in the present example, first syringe barrel (120) contains tissue morsels while second syringe barrel (122) contains fibrin scaffold material. Of course other fluids or treatment mixtures may be contained within syringe barrels (120, 122). As shown, dual-inlet assembly (140) joins the flows from first and second syringe barrels (120, 122) such that a single mixed flow is injected into distal chamber (130) from port (138). It should be understood that a variety of other devices and components may be used to introduce tissue morsels, a fibrin scaffold material or other type of scaffold material, and/or other liquids/materials into distal chamber (130), in addition to or in lieu of syringe assembly (108).

Distal chamber (130) of housing (102) comprises agitators (146) that are operable to further mix the injected tissue/fibrin fluid from port (138). As shown by the arrow in FIG. 3, the flow from port (138) travels around debriding shaft (104) before entering second access windows (148) of debriding shaft (104). Agitators (146) direct the flow of this tissue/fibrin mixture, and in the process increase mixing time and fluid flow turbulence to achieve a uniform tissue/fibrin mixture through a static mixing process before the tissue/fibrin flow enters second access windows (148). In the present example, agitators (146) are configured as helical, inwardly spiraling projections within distal chamber (130). Agitators (146) further are sized to be positioned adjacent the outer surface of debriding shaft (104) while still permitting the tissue/fibrin combination to flow distally to reach second access windows (148). In some versions, agitators (146) are provided about the exterior of debriding shaft (104) in addition to or in lieu of being provided on the sidewall defining distal chamber (130). In some such versions, the mixing process may be performed as an active process, such as by rotating housing (102) relative to debriding shaft (104). Other suitable structures and configurations for agitators (146) will be apparent to those of ordinary skill in the art in view of the teachings herein. In some versions, distal chamber (130) has a capacity of between approximately 10 cc's and approximately 30 cc's, though it should be understood that distal chamber (130) may have any other suitable capacity.

Second access windows (148) are positioned along debriding shaft (104) such that second access windows (148) reside within distal chamber (130) near the distal-most end of chamber (130). With this configuration, the fluid from port (138) is assured to pass through agitators (146) prior to entering second access windows (148). Second access windows (148) provide access to the interior of debriding shaft (104). Once the tissue/fibrin mixture enters the interior of debriding shaft (104), the mixture flows distally and exits debriding shaft (104) at apertures (116) to arrive at a treatment site. As shown in FIG. 3, first and second access windows (136, 148) are configured as longitudinal slots formed in the sidewall of debriding shaft (104). However, other suitable configurations for first and second access windows (136, 148) that may be used to transport fluid from proximal and distal chambers (128, 130) to apertures (116), and ultimately a treatment site, will be apparent to those of ordinary skill in the art in view of the teachings herein. For instance, among other configurations, longitudinal slots for first and second access windows (136, 148) could be replaced or supplemented by a plurality of circular holes. Additionally, access windows (148) may be made to open once syringe assembly (108) is engaged with housing (102) such that access windows (148) are closed during the debriding step. This may prevent debrided tissue from getting stuck in port (138).

As a merely illustrative variation, agitators (146) may be positioned within the hollow interior of debriding shaft (104) (e.g., instead of being within the hollow interior of housing (102)). For instance, agitators (146) may be longitudinally positioned between access windows (148) and apertures (116), within the hollow interior of debriding shaft (104). In some such versions, port (138) may be positioned directly over access windows (148). Furthermore, the hollow interior of debriding shaft (104) may be blocked just distal to the distal-most aperture (116). Such a configuration may minimize dead volume space. Of course, any other suitable features and structures may be used to agitate a tissue/fibrin mixture.

In the present example shown in FIG. 3, port (138) is connected with syringe assembly (108). Further, port (134) is configured for connection to a saline supply, e.g. via a conduit, separate syringe, etc. With device (100) fully assembled, both ports (134, 138) are connected to fluid sources such that fluid flow within device (100)—through proximal and distal chambers (128, 130)—is directed to apertures (116), which are open and thus permit fluid to flow from within debriding shaft (104) to a treatment site. In some other versions, port (138) may be configured with various types of valves to provide selective coupling of syringe assembly (108) to device (100) without fluid leaking from port (138) when syringe assembly (108) is not coupled to port (138). For instance, with a configuration using valves within port (138), saline could be injected within device (100) from port (134) without saline flowing through access windows (148) and out port (138) instead of flowing through apertures (116). With such a configuration using valves within port (138), port (138) may include one valve near the interface of port (138) with distal chamber (130); or port (138) may include one valve at each first and second inlet (142, 144) to provide selective coupling with either syringe assembly (108) or with separate syringes. Valves could even be positioned at all three locations. Port (138) may also include a luer lock feature to facilitate selective coupling of syringe assembly (108) with port (138). Valves (e.g., one-way flap valves) may also be provided at or near access windows (136, 148), permitting communication of fluid into the hollow interior of debriding shaft (104) but not out of the hollow interior of debriding shaft (104) via access windows (136, 148). Similarly, port (134) may be configured with various types of valves to provide selective coupling of an irrigating fluid supply, e.g. saline supply, to device (100) without a treatment fluid leaking from port (134) when the irrigating fluid supply is not coupled to port (134). For instance, with a configuration using a valve within port (134), a tissue/fibrin mix could be injected within device (100) from port (138) without the tissue/fibrin mix flowing out port (134) instead of apertures (116). Other suitable structures, features, and configurations for preventing backflow of fluid from ports (134, 138) will be apparent to those of ordinary skill in the art in view of the teachings herein.

In an exemplary use, device (100) is inserted into a treatment site (e.g., into a fistula), placing distal portion (112) of debriding shaft (104) at the treatment site. Central shaft (106) is then engaged with debriding shaft (104) and central shaft (106) rotated to cause debriding shaft (104) to rotate. As debriding shaft (104) rotates, cutters (114) on debriding shaft (104) rotate past tissue cells within the treatment site and debride the treatment site by removing tissues and cells (e.g., epithelial cells, etc.) to prepare the treatment site for receipt of a treatment mixture. Such rotation may be in both directions, such as through a rocking or oscillating motion. In addition to rotating, debriding shaft (104) device (100) may be reciprocated to ensure debriding occurs along the entire length of a treatment site. Still in some versions, debriding shaft (104) may also be configured with some degree of longitudinal translation to also promote debriding along the entire length of a treatment site.

After cutters (114) have removed tissue cells, the treatment site is cleansed by suctioning away debris using a suction device connected to port (134) and/or irrigating the site with saline injected through port (134) to flush debris (e.g., epithelial cells, etc.) from the treatment site. The injected saline enters proximal chamber (128) from port (134) and then enters the interior of debriding shaft (104) via first access windows (136). The injected saline travels distally, exiting apertures (116) to flush the treatment site. To the extent that this injection of saline into the interior of debriding shaft (104) floods distal chamber (130) by exiting second access windows (148), the presence of syringe assembly (108) and the lack of any other vent will still ultimately provide communication of the saline to apertures (116). Furthermore, second access windows (148) may include a valve (e.g., a one-way flap) to prevent leakage from the interior of shaft (104) into distal chamber (130) and thus to port (138). To ensure thorough cleaning of the treatment site, device (100) may be reciprocated and/or rotated during the suctioning and/or irrigating steps.

With the treatment site prepared, distal portion (112) of debriding shaft (104) is fully inserted within the treatment site, and syringe assembly (108) is actuated by depressing plunger actuator (125). A distal portion of housing (102) may also be inserted within the treatment site at this stage. The actuation of syringe assembly (108) sends a mixture of tissue morsels and fibrin scaffold material from syringe barrels (120, 122) into distal chamber (130). The tissue/fibrin mixture flows around debriding shaft (104) and past agitators (146), which further mix the fibrin and tissue morsels. The tissue/fibrin mixture eventually reaches second access windows (148) where the tissue/fibrin mixture then enters the interior of debriding shaft (104). Once within debriding shaft (104), the tissue/fibrin mixture flows distally and exits from apertures (116) at the treatment site. As the tissue/fibrin mixture exits apertures (116), device (100) is steadily withdrawn from the treatment site to ensure an appropriate quantity of tissue/fibrin mixture is delivered along the length of the treatment site. Other suitable ways in which device (100) may be used will be apparent to those of ordinary skill in the art in view of the teachings herein.

III. Exemplary Tissue Treatment Device with Distal Barbs

FIGS. 4-8 depict another exemplary tissue treatment device (200). Device (200) comprises a housing (202), a debriding shaft (204), a syringe assembly (208), and a syringe (209). These components and their sub-components will be described in greater detail below. As will also be described in greater detail below, tissue treatment device (200) may be used to debride a fistula and administer a therapeutic mixture of biological material to the fistula to treat the fistula. It should be understood, however, that tissue treatment device (200) may be used in a variety of other ways and in a variety of other settings and procedures.

As shown in FIGS. 4-8, debriding shaft (204) comprises distal portion (212) that extends from housing (202). Distal portion (212) comprises closed distal end (218) and a plurality of cutters (214) operable for removing tissues and cells from a treatment site (e.g., in a fistula, etc.) in preparation for the site to receive a treatment as will be discussed in greater detail below. Cutters (214) are configured as fins that protrude radially outwardly from debriding shaft (204). These protruding fins have sharpened edges that are operable to remove tissues and cells when device (200) is inserted to a treatment site and debriding shaft (204) is rotated and/or reciprocated as will be discussed in greater detail below. Distal end (218) of the present example is blunt, such that insertion of distal end (218) into an anatomical lumen (e.g., a fistula, etc.) will not inflict significant trauma on the sidewall of the anatomical lumen. Alternatively, distal end (218) may have a variety of other configurations, including but not limited to a sharp configuration. As another merely illustrative example, debriding shaft (204) may comprise an open or partially open distal end instead of having a closed distal end (218). Other suitable features, components, and configurations of debriding shaft (204) will be apparent to those of ordinary skill in the art in view of the teachings herein.

Syringe assembly (208) of the present example comprises a dual syringe barrel configuration. In the present example, first syringe barrel (220) contains prepared tissue morsels, while second syringe barrel (222) comprises fibrin scaffold material. Of course, first and second syringe barrels (220, 222) may contain other fluids or mixtures. To the extent that syringe assembly (208) contains tissue morsels, such tissue morsels may be formed or derived at least in part from tissue that was harvested from the same patient in which device (200) is being used to treat a medical condition (e.g., a fistula, etc.). Syringe assembly (208) is in fluid communication with the interior of housing (202) via a port (238), such that the tissue morsels and fibrin scaffold mix may be injected into the interior of housing (202) to produce a treatment mixture as will be described further below. Syringe assembly (208) further comprises a first plunger (221) that translates within first syringe barrel (220); and a second plunger (223) that translates within second syringe barrel (222). A plunger actuator (225) is unitarily secured to both plungers (221, 223), such that both plungers (221, 223) may be actuated simultaneously by actuating plunger actuator (225). In some other versions, plungers (221, 223) may be actuated independently of each other.

Syringe (209) of device (200) has a conventional single syringe configuration. In the present example, syringe (209) contains an irrigating fluid such as saline, etc. Of course, other fluids (e.g., a therapeutic fluid, etc.) may be contained in syringe (209) in addition to or in lieu of an irrigating fluid. Syringe (209) is in fluid communication with the interior of housing (202) via a port (234), such that the irrigating fluid may be injected into the interior of housing (202) to irrigate the treatment site as will be described in greater detail below.

Figure 6:
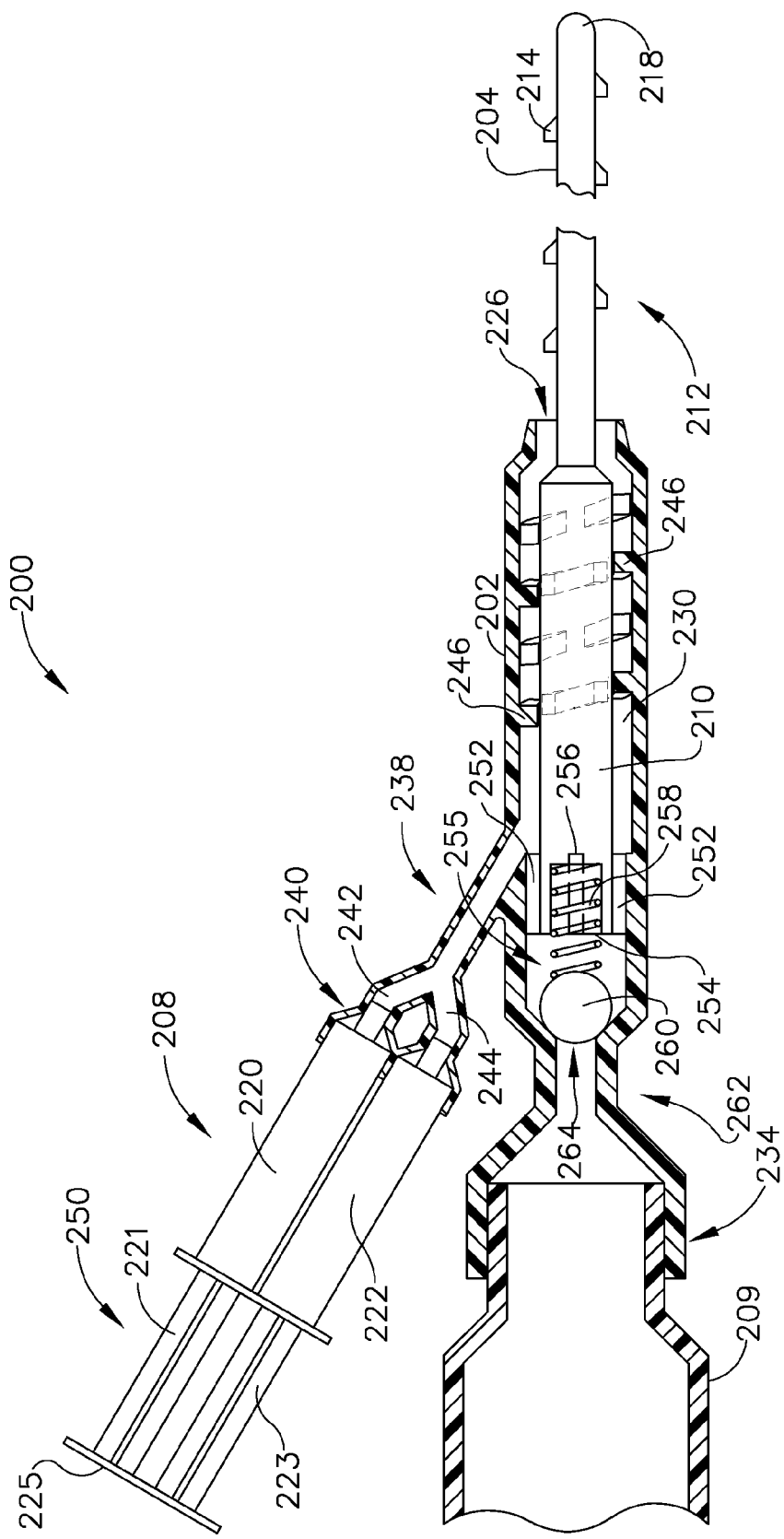
FIG. 6 depicts a first series side view of the device of FIG. 5, with the housing shown in cross section, and with the device shown in a debriding configuration.
Figure 7:
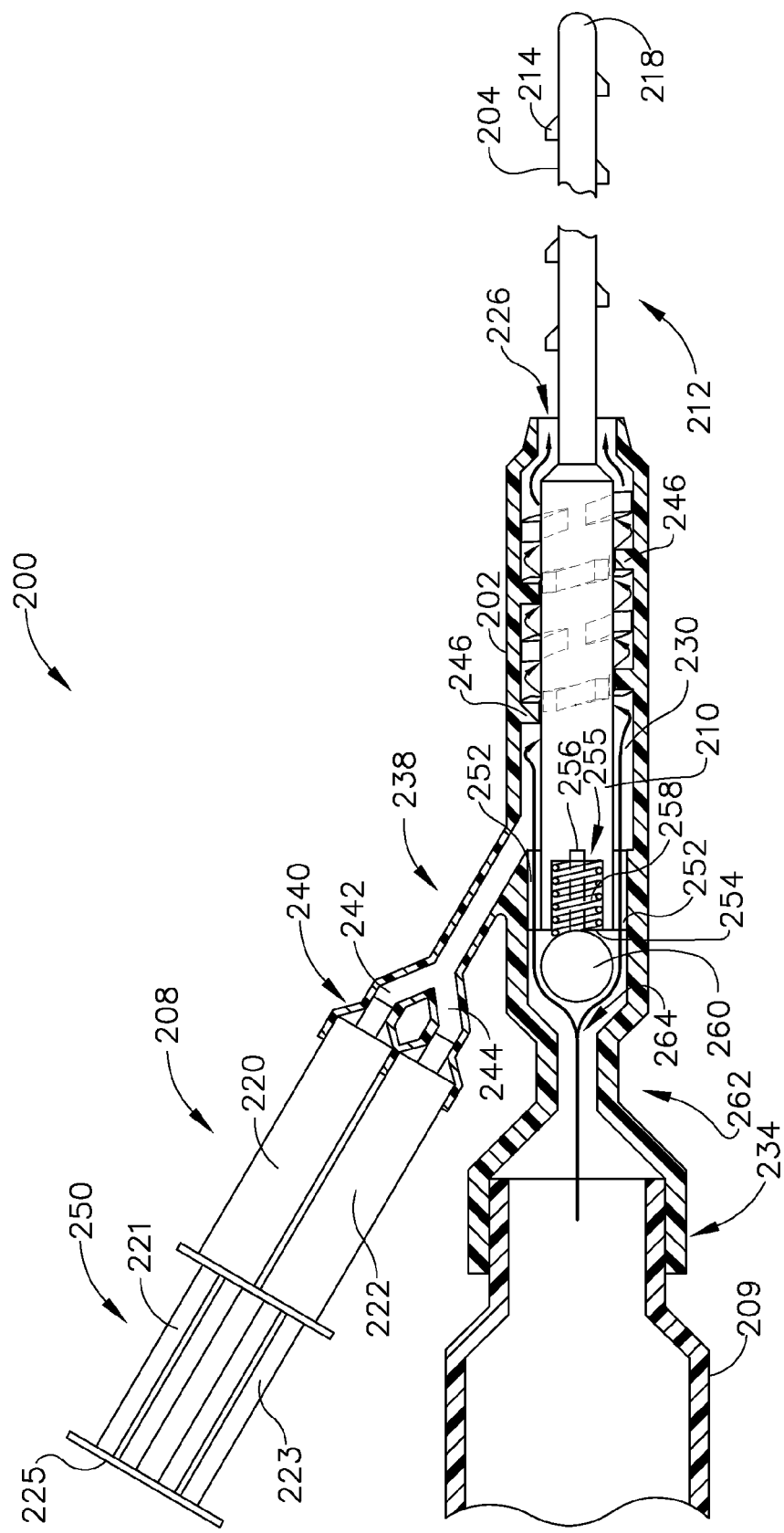
FIG. 7 depicts a second series side view of the device of FIG. 5, with the housing shown in cross section, and with the device shown in an irrigation configuration.
Figure 8:
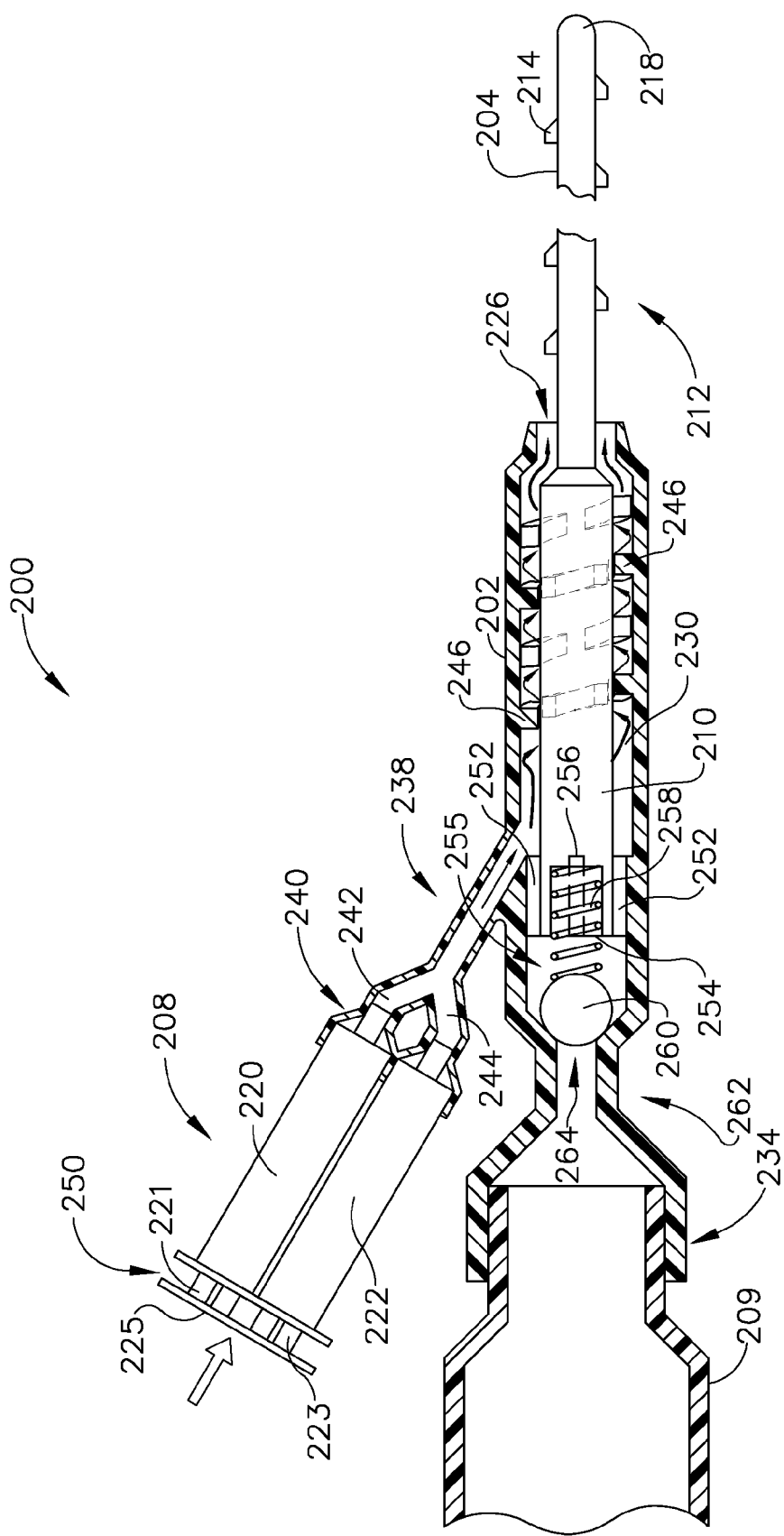
FIG. 8 depicts a third series side view of the device of FIG. 5, with the housing shown in cross section, and with the device shown in a treatment application configuration.

As seen in FIGS. 6-8, housing (202) of the present example comprises port (234), a restriction (262) downstream of port (234), a chamber (230), port (238), agitators (246), and an open distal end (226). Debriding shaft (204) comprises proximal portion (210) that extends proximally within housing (202) via open distal end (226). Proximal portion (210) of debriding shaft (204) is secured to the interior of housing (202) by flanges (252), though any other suitable structures or techniques may be used. Debriding shaft (204) may be movable relative to housing (202) in some alternative versions. Proximal portion (210) of debriding shaft (204) defines a recess (254) that houses a ball valve assembly (255). Ball valve assembly (255) comprises a spring rod (256), which is connected with a spring (258), and a ball (260), which is connected to the proximal-most end of spring (258). With device (200) assembled, ball (260) is resiliently biased by spring (258) to push toward restriction (262) of housing (202) to thereby seal chamber (230) of housing (202) from restriction (262), port (234), and syringe (209).

Port (234) of housing (202) is connected with syringe (209), which acts as an irrigating device for injecting fluid, e.g. saline, within and through chamber (230). Syringe (209) may itself contain a quantity of saline or other irrigating fluid; or port (234) may be coupled with a separate irrigating device containing saline or other irrigating fluid. When injecting saline within device (200), syringe (209) may include a plunger that is depressed to inject saline; or saline may be transported through port (234) by a pump associated with the separate irrigating device. Other suitable ways to deliver an irrigating fluid from syringe (209) to device (200) will be apparent to those of ordinary skill in the art in view of the teachings herein. For instance, in some versions syringe (209) may be replaced by a conduit connected to a pressurized fluid supply or gravity-fed fluid supply, etc.

Chamber (230) of housing (202) is coupled with syringe assembly (208) by port (238). In the present example, port (238) branches into a dual-inlet assembly (240), where first inlet (242) is configured to receive first syringe barrel (220) and second inlet (244) is configured to receive second syringe barrel (222). As mentioned previously, in the present example, first syringe barrel (220) contains tissue morsels while second syringe barrel (222) contains fibrin scaffold material. Of course other fluids or treatment mixtures may be contained within syringe barrels (220, 222). As shown, dual-inlet assembly (240) joins the flows from first and second syringe barrels (220, 222) such that a single mixed flow is injected into chamber (230) from port (238). It should be understood that a variety of other devices and components may be used to introduce tissue morsels, a fibrin scaffold material or other type of scaffold material, and/or other liquids/gels/materials into chamber (230), in addition to or in lieu of syringe assembly (208).

Chamber (230) of housing (202) comprises agitators (246) that are operable to further mix the injected tissue/fibrin flow from port (238). As shown by the arrows in FIG. 8, the flow from port (238) travels around debriding shaft (204) and between debriding shaft (204) and agitators (246) before exiting open distal end (226). Agitators (246) direct the flow of this tissue/fibrin mixture, and in the process increase mixing time and fluid flow turbulence to achieve a uniform tissue/fibrin mixture through a static mixing process before the tissue/fibrin flow exits housing (202) via open distal end (226). In the present example, agitators (246) are configured as helical, inwardly spiraling projections within chamber (230). Agitators (246) further are sized to be positioned adjacent the outer surface of debriding shaft (204) while still permitting the tissue/fibrin combination to flow distally to exit housing (202) via open distal end (226). In some versions, agitators (246) are provided about the exterior of proximal portion (210) of debriding shaft (204) in addition to or in lieu of being provided on the sidewall defining chamber (230). In some such versions, the mixing process may be performed as an active process by rotating debriding shaft (204) within housing (202). Other suitable structures and configurations for agitators (246) will be apparent to those of ordinary skill in the art in view of the teachings herein. In some versions, chamber (230) has a capacity of between approximately 10 cc's and approximately 30 cc's, though it should be understood that chamber (230) may have any other suitable capacity.

In the present example, port (238) is coupled with syringe assembly (208), and port (234) is coupled with syringe (209). With device (200) fully assembled, both ports (234, 238) are coupled with fluid sources such that fluid flow within device (200) is directed distally toward open distal end (226) of housing (202), which is not sealed and thus permits fluid to flow from within chamber (230) to a treatment site. Furthermore, ball valve assembly (255) is operable to seal syringe (209) from chamber (230) when saline, or another irrigating fluid, is not being injected to device (200). Ball valve assembly (255) thus ensures fluid flow from syringe assembly (208) cannot backflow into restriction (262), port (234), or syringe (209). In some other versions, port (238) is configured with a valve to ensure fluid flow from syringe (209) cannot backflow into port (238) or syringe assembly (208). With configurations using various types of valves to seal off ports (234, 238), syringe assembly (208) and syringe (209) may be selectively attached with port (238) and port (234) respectively such that the various syringes may be separated from device (200) when in use until needed. Other suitable structures and configurations for device (200) for preventing backflow of fluid from ports (234, 238), and/or for providing selective connection of syringe assembly (208) and syringe (209) with port (238) and port (234) respectively, will be apparent to those of ordinary skill in the art in view of the teachings herein.

FIGS. 6-8 show a series view of device (200) during different stages of an exemplary treatment preparation and application process. In particular, FIG. 6 shows device (200) in a debriding configuration. In this configuration, ball (260) is pressed against distal opening (264) of restriction (262), thereby substantially sealing off chamber (230) from syringe (209). In this configuration, device (200) is inserted into a treatment site (e.g. into a fistula), placing distal portion (212) of debriding shaft (204) at the treatment site. With debriding shaft (204) at the treatment site, device (200) is rotated and/or reciprocated manually, causing cutters (214) to debride the treatment site by removing tissue cells (e.g., epithelial cells, etc.) to prepare the treatment site for receipt of a treatment mixture. While the present example uses manual rotation and/or reciprocation to debride the treatment site, similar motorized actions could be used in addition to or in lieu of manual rotation and/or reciprocation, to achieve debriding.

After cutters (214) have removed tissues and cells, the treatment site is ready for cleansing by irrigating the site with saline or other suitable irrigating fluid. Referring now to FIG. 7, syringe (209) is actuated as described above to initiate and ultimately inject the saline through port (234), through restriction (262), and through chamber (230) to the treatment site. The pressure exerted on ball (260) by the saline from syringe (209) is sufficient to overcome the bias of spring (258), thereby causing spring (258) to compress within recess (254) of debriding shaft (204). With spring (258) compressed, saline flows around ball (260), through chamber (230), past agitators (246), and out open distal end (226) of housing (202) to the treatment site, as shown by the arrow in FIG. 7. It should be understood that, at this stage, at least part of housing (202) may be inserted in (or at least be adjacent to) the treatment site (e.g., within a fistula tract, etc.) to provide satisfactory irrigation or flushing of the site. When the site is sufficiently irrigated or flushed, the saline flow is ceased and the bias of spring (258) restores ball (260) to its initial position—substantially sealing distal opening (264) of restriction (262). To ensure thorough cleaning of the treatment site, device (200) may be reciprocated and/or rotated during such irrigating or flushing.

With the treatment site prepared, debriding shaft (204) and at least a distal portion of housing (202) is fully inserted within the treatment site, and syringe assembly (208) is actuated by depressing plunger actuator (225) as shown in FIG. 8. This actuation of syringe assembly (208) sends a mixture of tissue morsels and fibrin scaffold material from syringe barrels (220, 222) into chamber (230). The tissue/fibrin mixture flows around debriding shaft (204) and past agitators (246), which further mix the fibrin an tissue morsels. The tissue/fibrin mixture eventually reaches open distal end (226) of housing (202) where the tissue/fibrin mixture then exits device (200) into the treatment site (e.g., into the fistula tract, etc.). As the tissue/fibrin mixture exits open distal end (226) of housing, device (200) is steadily withdrawn from the treatment site to ensure an appropriate quantity of tissue/fibrin mixture is delivered along the length of the treatment site. Other suitable ways in which device (200) may be used will be apparent to those of ordinary skill in the art in view of the teachings herein.

IV. Miscellaneous

While the foregoing examples use fibrin as a scaffold material to be combined with tissue morsels, it should be understood that a variety of other types of materials may be used to provide a scaffold for tissue morsels and/or to be otherwise mixed with tissue morsels. By way of example only, the fibrin scaffold material referred to in the above examples may be substituted or supplemented with a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven Vicryl® (Ethicon, Inc., Somerville, N.J.), monocryl material, fibrin, non-woven poly-L-lactide, and non-woven panacryl (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly (ether urethane), and blends and copolymers thereof. Suitable synthetic polymers for use in the present invention can also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides and combinations thereof. Furthermore, any other medical fluid component (or combinations thereof) referred to herein may be combined with tissue morsels. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for use in preparing a tissue site for treatment and applying a treatment to the tissue site, wherein the device comprises:
   (a) a housing comprising:
      (i) a first fluid chamber,
      (ii) a first port in communication with the first fluid chamber, wherein the first port is configured to transmit a first fluid from a first fluid dispensing device to the first fluid chamber, and
      (iii) a plurality of agitators extending inwardly from an interior surface of the first fluid chamber toward a central longitudinal axis of the first fluid chamber, wherein the agitators define a longitudinal passage; and
   (b) a debriding shaft having a proximal portion extending longitudinally within the first fluid chamber of the housing and a distal portion extending longitudinally from a distal end of the housing, wherein the debriding shaft passes through the longitudinal passage, wherein the debriding shaft comprises:
      (i) a plurality of cutting members spaced along the distal portion of the debriding shaft, wherein the cutting members project from the debriding shaft, wherein the debriding shaft comprises at least one aperture defined by an exterior surface of the debriding shaft and an interior surface of at least one cutting member of the plurality of cutting members, and
      (ii) a first plurality of openings radially disposed within a proximal portion of the debriding shaft distally of the plurality of agitators, wherein the first plurality of openings is on an exterior surface of the debriding shaft within the first fluid chamber, wherein the first plurality of openings provides access to a hollow interior portion of the debriding shaft, and wherein the hollow interior portion of the debriding shaft is in further communication with the at least one aperture.

2. The device of claim 1, further comprising:
   (a) a second fluid chamber; and
   (b) a second port in communication with the second fluid chamber, wherein the second port is configured transmit a second fluid from a second fluid dispensing device to the second fluid chamber.

3. The device of claim 2, wherein the second fluid chamber is proximal from the first fluid chamber, wherein the debriding shaft extends longitudinally within the second fluid chamber.

4. The device of claim 3, wherein the debriding shaft comprises a second plurality of openings within a portion of the debriding shaft located within the second fluid chamber, wherein the second plurality of openings provides access to the hollow interior portion of the debriding shaft such that the second plurality of openings is in communication with the at least one aperture.

5. The device of claim 4, wherein the first and second plurality of openings of the debriding shaft comprise longitudinal slots.

6. The device of claim 2, wherein the second fluid from the second fluid dispensing device comprises saline.

7. The device of claim 1, wherein first port comprises a first inlet and a second inlet, wherein the first fluid dispensing device comprises dual syringe barrels, wherein each of the dual syringe barrels is associated with a select one of the first and second inlets.

8. The device of claim 7, further comprising a tissue material contained within a first one of the syringe barrels and a scaffold material contained within a second one of the syringe barrels.

9. The device of claim 1, wherein the plurality of agitators comprise a spiral member.

10. The device of claim 1, wherein the plurality of agitators are static.

11. The device of claim 1, wherein the debriding shaft is selectively keyed to the housing.

12. The device of claim 1, wherein each of the cutting members of the plurality of cutting members defines an aperture in communication with the hollow interior portion of the debriding shaft.

13. The device of claim 1, wherein the debriding shaft has a closed distal end.

14. An instrument for debriding tissue and applying therapeutic cells, wherein the instrument comprises:
 (a) a housing comprising:
  (i) a first fluid chamber,
  (ii) a first port in communication with the first fluid chamber, wherein the first port is operably configured to transmit a first fluid to the first fluid chamber,
  (iii) a second fluid chamber positioned proximally of the first fluid chamber,
  (iv) a second port in communication with the second fluid chamber, wherein the second port is operably configured to transmit a second fluid to the second fluid chamber, and
  (v) a plurality of agitators projecting inwardly from an interior surface of the first fluid chamber, wherein the first port is positioned proximally of the agitators; and
 (b) a debriding shaft passing longitudinally through the first fluid chamber and the second fluid chamber, wherein the plurality of agitators are positioned adjacent to an exterior surface of the debriding shaft, wherein the debriding shaft comprises a proximal portion secured within the housing and a distal portion extending from the housing, wherein the distal portion of the debriding shaft presents a plurality of debriding features operable to debride tissue, wherein the debriding shaft further comprises a first plurality of openings and a second plurality of openings, wherein the first plurality of openings are disposed within a portion of the debriding shaft distally of the plurality of agitators within the first fluid chamber, and wherein the second plurality of openings are disposed within a portion of the debriding shaft within the second fluid chamber.

15. The instrument of claim 14, wherein the valve comprises a spring and a ball, wherein the ball is connected to a proximal end of the spring, wherein the spring is biased to drive the ball in a proximal direction to seal the fluid chamber from the second port.

16. The instrument of claim 14, wherein the plurality of agitators comprise a spiral member positioned adjacent the proximal portion of the debriding shaft extending within the housing.

17. The instrument of claim 14, further comprising a first injector coupled with the first port and a second injector coupled with the second port.

* * * * *